(12) United States Patent
Englebienne et al.

(10) Patent No.: US 6,808,936 B1
(45) Date of Patent: Oct. 26, 2004

(54) METHODS AND COMPOSITIONS FOR USE IN THE DIAGNOSIS AND TREATMENT OF CHRONIC IMMUNE DISEASE

(75) Inventors: Patrick Englebienne, Zingem (BE); Kenny Leo De Meirleir, Mechelen (BE); Charles Vincent Herst, Oakland, CA (US)

(73) Assignee: R.E.D. Laboratories, N.V., Zellik (BE)

( * ) Notice: Subject to any disclaimer, the term of this patent is extended or adjusted under 35 U.S.C. 154(b) by 233 days.

(21) Appl. No.: 09/645,071

(22) Filed: Aug. 23, 2000

(51) Int. Cl.[7] .............................................. G01N 33/564
(52) U.S. Cl. ............................ 436/506; 435/4; 435/7.1; 435/29
(58) Field of Search .......................................... 435/29

(56) References Cited

U.S. PATENT DOCUMENTS

| | | |
|---|---|---|
| 5,766,859 A | 6/1998 | Vojdani et al. |
| 5,776,690 A | 7/1998 | Vojdani et al. |
| 5,830,668 A | 11/1998 | Mordechai et al. |
| 5,853,996 A | 12/1998 | Mordechai et al. |
| 5,985,565 A | 11/1999 | Suhadolnik |
| 6,080,554 A | 6/2000 | Campine et al. |
| 6,130,206 A | 10/2000 | Carter |

FOREIGN PATENT DOCUMENTS

| | | |
|---|---|---|
| WO | WO 91/00097 | 1/1991 |

OTHER PUBLICATIONS

The Merch Manual of Diagnosis and Therapy, 2000.*
Diaz–Guerra, "Activation of the IFN–Inducible Enzyme RNase L Causes Apoptosis of Animal Cells" Academic Press, *Virology* 236, 354–363 (1997), Article No., VY978719.
Castelli, "A Study of the Interferon Antiviral Mechanism: Apoptosis Activation by the 2–5A System" *The Journal of Experimental Medicine*, vol. 186, No. 6, Sep. 15, 1997 967–972.

* cited by examiner

*Primary Examiner*—Patrick J. Nolan
(74) *Attorney, Agent, or Firm*—Bret E. Field; Bozicevic, Field & Francis LLP

(57) ABSTRACT

Methods and compositions are provided for use in the diagnosis and treatment of a host suffering from a chronic immune disease. In the diagnostic methods of the subject invention, a host derived sample, typically PBMC or a derivative thereof is assayed for the presence of low molecular weight fragments of RNase L, typically in conjunction with an evaluation of caspase activity. The results of this assay are then employed to diagnose and/or characterize a chronic immune disease in the host. In the treatment methods of the subject invention, an effective amount of agent capable of enhancing RNase L homodimer activity in the host, e.g., in host PBMC, is administered to the host. Also provided are methods for identifying agents having RNase L cleavage-inhibitory activity or RNase L fragment antagonist activity.

7 Claims, 4 Drawing Sheets

Fragment #1
(NF-kB mimicry)

Fragment #2
(2'-5'A Binding)

Fragment #3
(Cdk6 chain A mimicry)

Figures 2A to 2C. Three Dimensional Representations of Three RNase L Fragments Involved in Anti-Apoptosis in PBMCs of CFS Patients

Figure 4

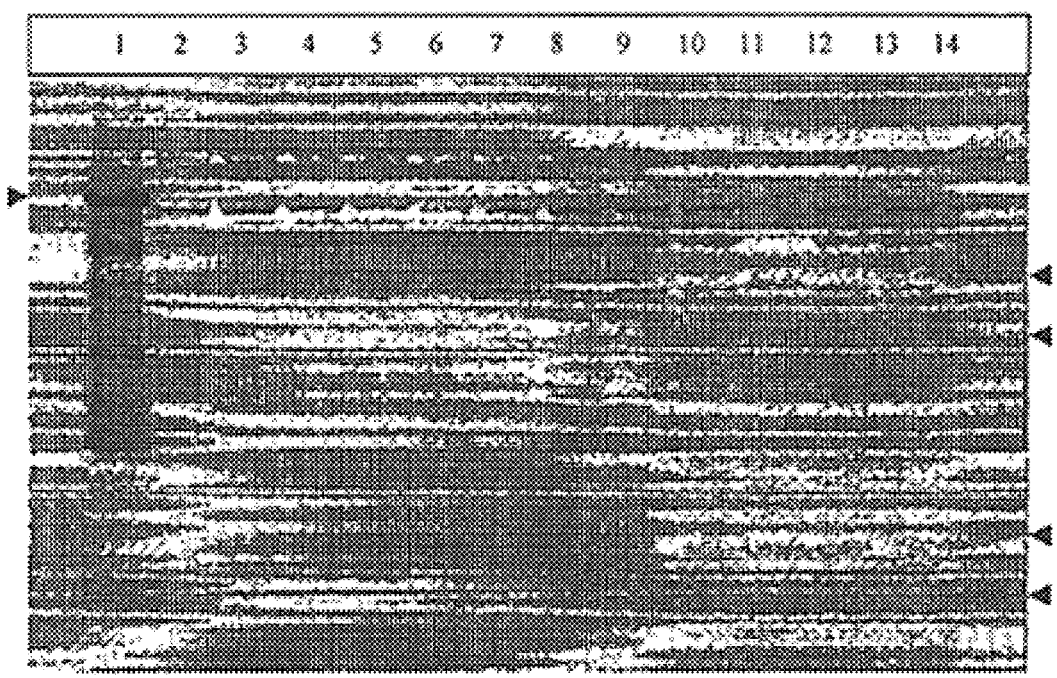

Figure 4. Western Blot Analysis of PBMC Extracts for RNase L Protein and Related Fragments in Healthy Controls and CFS Patients Before and After Therapy with Mismatched dsRNA. Lane 1 – recombinant RNase L; Lanes 2, 3, 4, and 5 – Healthy controls; Lane 6 – Patient A before therapy; Lane 7 – Patient A after therapy; Lane 8 – Patient B before therapy; Lane 9 – Patient B after therapy; Lane 10 – Patient C before therapy; Lane 11 – Patient C after therapy; Lane 12 – Patient D before therapy; Lane 13 – Patient D after therapy; Lane 14 – Patient D after cessation of therapy for six months. [Arrow to left indicates 80 kDa native RNase L. Arrows to right indicate
RNase L-related fragments visible in Lanes 6, 8, 10, 11, 12, and 14. Approximate molecular weights (from top to bottom) are: 65 kDa, 55 kDa, 37 kDa, and 30 kDa]

METHODS AND COMPOSITIONS FOR USE IN THE DIAGNOSIS AND TREATMENT OF CHRONIC IMMUNE DISEASE

TECHNICAL FIELD

The field of this invention is chronic immune disease, particularly chronic fatigue syndrome and multiple sclerosis.

BACKGROUND OF THE INVENTION

Chronic immune diseases can be highly debilitating. Two such chronic immune diseases are multiple sclerosis and chronic fatigue syndrome.

Multiple sclerosis (MS) is a neurological illness of unknown etiology associated with attacks of focal or multifocal neurological dysfunction arising from lesions within the central nervous system (CNS). In America and Northern Europe, MS is the most common neurological disease, with prevalence rates estimated between 50–100 per 100,000 population. The onset of disease is most common in early adulthood. Recurrent attacks can occur over many years, with approximately 30 percent of the patients progressing to a severe form of the disease which can be fatal.

MS is pleomorphic in its presentation. The clinical manifestations are determined in part by the location of the foci of demyelination within the CNS. Classical features of the disease include impaired vision, nystagmus, dysarthia, ataxia and intention tremor, and weakness/paralysis of one or more limbs.

The most common form of the disease is episodic. Symptoms develop with subsequent recovery, then another attack occurs. In approximately 50 percent of all patients with MS, attacks become more frequent, usually with a worsening of symptomatology. In 30 percent of all patients, the disease develops into what is referred to as progressive/relapsing, the most severe form of the disease. In this state remissions are rare and patients frequently become wheelchair bound.

The characterization of MS disease activity (including diagnosis, determination of disease state, monitoring of disease progression, prediction of disease attacks, and the like), remains problematic. To aid the clinician, the only laboratory test available is testing the cerebrospinal fluid for oligoclonal bands, present in approximately 90 percent of all patients. Examination of the brain for demyelinating plaques, using magnetic resonance imaging (MRI) is useful but expensive, and is not warranted except in a small group of patients in which all other clinical and laboratory tests are negative. Furthermore, there is no diagnostic laboratory test to determine if a patient is having an attack, to monitor the progress of the attack, to determine if the patient is progressing to a more active form of the disease (i.e., progressive/relapsing), etc. Finally, there is no laboratory test available as a prognostic indicator and/or capable of monitoring the course of therapy. One commentator has summarized the situation as follows: "The need for reliable markers of disease activity in multiple sclerosis (MS) to better guide basic research, diagnosis, treatment, and monitoring therapy is well-recognized." Laman et al. (1998), *Mult. Scler.* 4:266–269.

Like MS, chronic fatigue syndrome (CFS) is an illness of unknown etiology. CFS is often associated with sudden onset, flu-like symptoms, debilitating fatigue, low-grade fever, myalgia and neurocognitive dysfunction. CFS patients typically display reduced Karnofsky performance scores (KPS). The Karnofsky performance test measures an individual's ability to function and carry on normal activities. Karnofsky scores range form zero for a nonfunctional or dead patient to 100 for a completely normal function.

Diagnosis of CFS remains one of exclusion. An accumulating body of evidence suggests that CFS is associated with disregulation of both humoral and cellular immunity, including mitogen response, reactivation of viruses, abnormal cytokine production, diminished natural killer cell function and changes in intermediary metabolites. It has been suggested that the clinical and immunological abnormalities observed in CFS might include defects in the double-stranded RNA (dsRNA)dependent, interferon-inducible pathways, i.e., the 2',5'-oligoadenylate (2-5A or 2 5 A) synthetase/RNase L and p68 kinase (PKR) antiviral defense pathways (Suhadolnik et al. (1994), *Clin. Infect. Dis.* 18:S96–S104; Suhadolnik et al. (1994), *In Vivo* 8:599–604). The 2 5 A synthetase/RNase L pathway is part of the antiviral defense mechanism in mammalian cells; this pathway also has a role in the regulation of cell growth and differentiation (Lengyel, (1982), *Ann. Review Biochem.* 51:251–282; Sen et al. (1 993), *Adv. Virus Res.* 42:57–102).

When activated by dsRNA, 2 5 A synthetase converts ATP to 2',5'-linked oligoadenylates with 5'-terminal phosphates. Biologically active 2 5 A binds to and activates a latent endoribonuclease, RNase L, which hydrolyzes single-stranded viral and cellular RNA, primarily after UpNp sequences, thereby inhibiting protein synthesis.

Previous studies on the 2 5 A synthetase/RNase L pathway in CFS revealed a statistically significant dysregulation in which the 2 5 A synthetase is present predominantly in its activated form, bioactive 2 5 A levels are elevated, and RNase L activity is upregulated (Suhadolnik et al., Clin. Infect. Dis., supra; Suhadolnik et al., In Vivo, supra). Expression of the serine-threonine kinase, PKR, is down-regulated in CFS (Suhadolnik et al., In Vivo, supra). PKR controls initiation of protein translation through phosphorylation of eIF-2.

Despite these efforts, a clear cut molecular marker for CFS has not been identified. What is needed is a biochemical test, relying on an unambiguous molecular marker for CFS, which may form the basis of a definitive CFS diagnosis.

As the above discussion demonstrates, currently employed methods of diagnosing and/or characterizing MS or CFS disease activity in a subject are inadequate. As such, there is a continued need in the field to develop additional means for diagnosing and/or characterizing MS or CFS disease activity in a subject.

In addition, an effective cure for either MS or CFS has yet to be developed. As such, there is continued interest in the identification of new treatment protocols for chronic immune diseases, and particularly for MS and CFS.

Relevant Literature

U.S. Patents of interest include: U.S. Pat. Nos. 5,766,859; 5,776,690; 5,830,668; 5,853,996; and 5,985,565. Also of interest is WO 91/00097. Other references of interest include: Castelli et al. (1997), *J. Exp. Med.* 186:967–972 and Diaz-Guerra et al. (1997), *Virology* 236:354–363.

SUMMARY OF THE INVENTION

Methods and compositions are provided for use in the diagnosis and treatment of a host suffering from a chronic immune disease. In the diagnostic methods of the subject invention, a host derived sample, typically PBMC or a derivative thereof, is assayed for the presence of low molecular weight fragments of RNase L, typically in conjunction with an evaluation of caspase activity. The results of this assay are then employed to diagnose and/or characterize a chronic immune disease in the host. In the treatment methods of the subject invention, an effective amount of agent capable of enhancing RNase L homodimer activity in the host, e.g., in host PBMC, is administered to the host Also provided are methods for identifying agents having RNase L cleavage-inhibitory activity, i.e, agents that inhibit the cleavage of RNase L, or RNase L fragment antagonist activity.

BRIEF DESCRIPTION OF THE FIGURES

FIG. 4 provides a Western blot analysis of PBMC extracts for RNase L protein and related fragments in healthy controls and CFS patients before and after therapy with mismatched dsRNA.

DESCRIPTION OF THE SPECIFIC EMBODIMENTS

Figure 1:
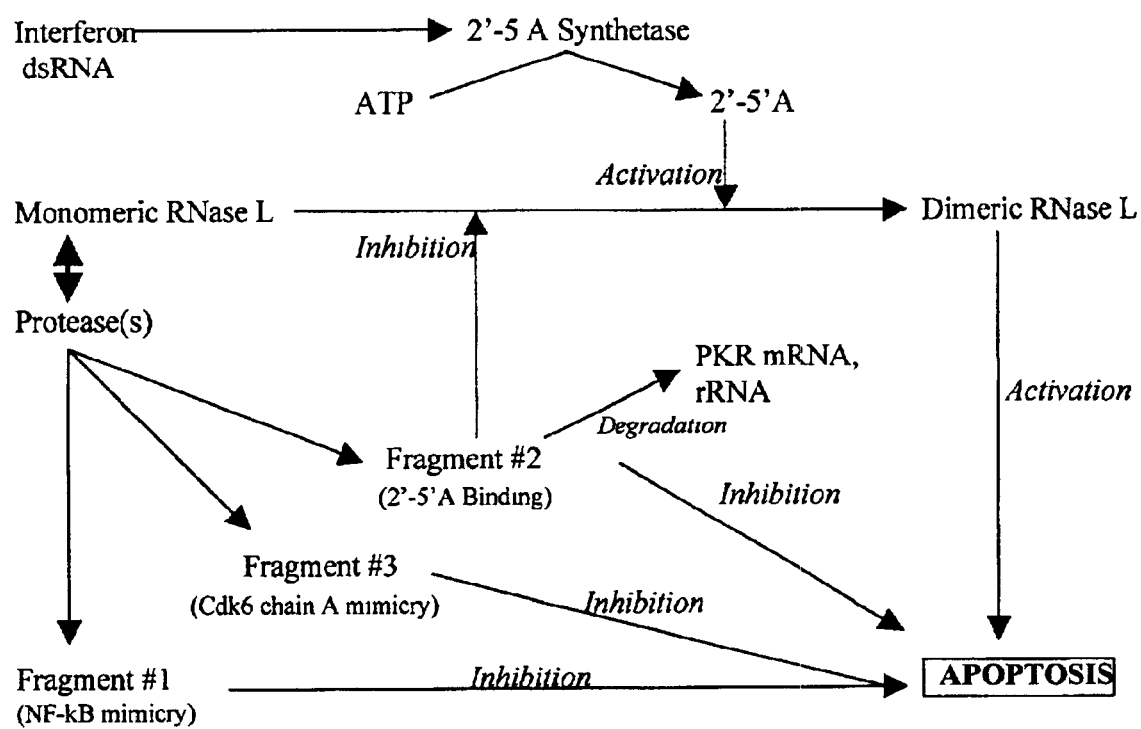
FIG. 1 provides a diagram showing the role of RNase L in CFS pathogenesis.

Methods and compositions are provided for use in the diagnosis and treatment of a host suffering from a chronic immune disease. In the diagnostic methods of the subject invention, a host derived sample, typically PBMC or a derivative thereof, is assayed for the presence of low molecular weight fragments of RNase L, typically in conjunction with an evaluation of caspase activity. The results of this assay are then employed to diagnose and/or characterize a chronic immune disease in the host. In the treatment methods of the subject invention, an effective amount of an agent capable of enhancing RNase L homodimer activity in the host, e.g., in host PBMC, is administered to the host. Also provided are methods for identifying agents having RNase L cleavage-inhibitory activity or RNase L fragment antagonist activity. In further describing the subject invention, the subject diagnostic/characterization methods will be described first, followed by a description of the subject treatment protocols and the screening methods.

Before the subject invention is described further, it is to be understood that the invention is not limited to the particular embodiments of the invention described below; as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Diagnostic/Characterization Methods

As summarized above, the subject invention provides methods of diagnosing and/or characterizing a chronic immune disease in a host. In other words, the subject invention provides methods for determining whether a host suffers from a chronic immune disease and/or characterizing or evaluating the state of the chronic immune disease inflicting the host.

In determining whether a host suffers from a chronic immune disease according to the subject invention, a sample from the host is assayed for the presence of one or more low molecular weight fragments of RNase L. By low molecular weight RNaseL fragment is meant a polypeptide that has a sequence of amino acid residues found in full length RNaseL, where this sequence is at least about 10, usually at least about 20 and more usually at least about 50 residues long and is often longer, where the polypeptide has a molecular weight that is less than that molecular weight of full length RNaseL, i.e., where the polypeptide has a molecular weight that is less than about 80 kDa, as measured by, SDS-PAGE. Specifically, the sample is assayed for low molecular weight RNaseL fragments ranging in weight from about 5 to 60 kDa, usually from about 5 to 50 kDa and more usually from about 5 to 45 kDa Of particular interest in many embodiments is the identification of one or more, usually two or three, of the following specific RNase L fragments having the following molecular weights: (a) fragment 1, molecular weight ranging from about 5 to 15, usually from about 7.5 to 12.5 and more usually from about 8 to 10 kDa, where this fragment typically comprises all or substantially all of residues 1 to 83 of the full length protein, where by substantially all is meant at least about 80, usually at least about 90 and more usually at least about 95% (See FIG. 2A); (b) fragment 2, molecular weight ranging from about 30 to 50, usually from about 35 to 45 and more usually from about 37.5 to 42.5 kDa, where this fragment typically comprises all or substantially all of residues 84 to 300 and 604 to 741 of the fill length protein, where by substantially all is meant at least about 80, usually at least about 90 and more usually at least about 95% and this fragment typically retains 2 5 A binding activity and RNaseL catalytic activity (See FIG. 2B); and (c) fragment 3, molecular weight ranging from about 25 to 40, usually from about 25 to 35 and more usually from about 30 to 35 kDa, where this fragment typically comprises all or substantially all of residues 301 to 603 of the full length protein, where by substantially all is meant at least about 80, usually at least about 90 and more usually at least about 95% (See FIG. 2C).

In certain embodiments, the methods further comprise a caspase activity assay, in which the caspase activity of one or more specific caspases in the sample is determined; where the presence of one or more caspase activities is indicative of the presence of the chronic immune disease of interest. Caspases of particular interest include: caspase 2, caspase 3, caspase 6, caspase 8 and caspase 9. The activities of these specific caspases can be assayed using any convenient protocol, where particular protocols of interest include those performed with the following commercially available assay kits: "the ApoTarget Caspase Assay (BioSource International); BioMol Quantizyme Assay System (BioMol Research Laboratories Inc.); and the Roche Caspase Assay System (Roche Molecular); and the like. Caspase assays are also described in: Hakem et al. (1998), *Cell* 94:339–352 and Slee et al. (1999), *J. Cell Biol.* 144:281–292. Representative caspase activity assays are presented in the Experimental Section, below.

The presence (or absence) of the low molecular weight RNase L fragments 1 to 3, and optionally the caspase activity data, is then used to diagnose whether or not the host suffers from the chronic immune disease. In other words, the presence or absence of low molecular weight RNaseL fragments in the sample is used to determine whether or not the host suffers from a chronic immune disease, such as CFS or MS, with the presence of such fragments being associated with the presence of the chronic immune disease and the absence of such fragments indicating that the host does not suffer from a chronic immune disease. For example, in one embodiment, the presence of one or more low molecular weight RNaseL fragments, e.g., fragment 1, 2 and/or 3, is used to determine whether the host suffers from CFS. Likewise, in another embodiment, the presence of one or more low molecular weight RNaseL fragments, e.g., fragment 1, 2 and/or 3, is used to determine whether a host suffers from MS. In certain embodiments, the ratio of one or more of the above specific fragments, e.g., fragment 1, 2 or 3, with respect to native RNase L present in the sample is determined and employed in the diagnostic step of the subject methods, as described in greater detail infra. As mentioned above, the diagnostic assay typically further includes an evaluation of caspase activity in many embodiments. In those embodiments where fragment 2 is the only fragment assayed for in the sample, the diagnostic assay typically further includes an evaluation of caspase activity. As part of the diagnosis, one may also evaluate the subject for other symptoms of the disease of interest which is to be diagnosed, e.g., the MS or CFS symptoms described in the background section, supra, as well as in other parts of this application.

Also provided by the subject invention are methods of characterizing the chronic immune disease activity, e.g., CFS or MS disease activity, in a subject suspected of having, or known to have, a chronic immune disease, e.g., CFS or MS. Subjects suspected of having, or known to have, a chronic immune disease and thus amenable to the subject methods can be identified using any convenient protocol. One convenient protocol is diagnosis based on clinical symptoms. A number of different clinical symptoms may be used to identify subjects that may have or have the chronic immune disease of interest, where the specific symptoms employed will necessarily depend on the specific chronic immune disease. For example, where the chronic immune disease of interest is CFS, clinical symptoms of interest include: fatigue of six months or longer that causes a reduction in effort of greater than 50 percent of normal output, athralgia, myalgia, sore throat accompanied by swollen glands, cognitive dysfunction (e.g. memory loss); and the like. For MS, clinical symptoms include: weakness of the limbs; sensory symptoms, e.g. paresthesia or hypesthesia; ataxia; optic neuritis; diplopia; trigeminal neuralgia; facial paralysis; vertigo; urinary or bowel movement abnormalities; and cognitive dysfunction, e.g., memory loss, impaired attention, problem-solving difficulties, slowed information processing, and difficulty in shifting between cognitive tasks. The presence of one or more of the above symptoms may be used to identify subjects suspected of suffering from CFS or MS, respectively. Other assays may also be employed, including MRI imaging, the oligoclonal band assay described in greater detail infra, etc.

The first step of the subject methods is to obtain a suitable sample from the subject or patient of interest, i.e., a patient suspected of having or known to have the chronic immune disease of interest, e.g., CFS or MS. The sample is derived from any initial source that contains the low molecular weight RNaseL fragments (if present). Sample sources of interest include, but are not limited to, many different physiological sources, e.g., CSF, urine, saliva, tears, tissue derived samples, e.g., homogenates, and blood or derivatives thereof.

In many embodiments, the sample is derived from cells that comprise the RNaseL, fragments of interest, if present—i.e., if the patient from which the cells are derived has chronic immune disease. In other embodiments, the sample may be derived from fluids into which the proteins/peptides of interest have been released, e.g., are present. In many embodiments, a suitable initial source for the patient sample is blood. As such, the sample employed in the subject assays of these embodiments is generally a blood derived sample. The blood derived sample may be derived from whole blood or a fraction thereof, e.g., serum, plasma, etc., where in many embodiments the sample is derived from blood cells harvested from whole blood. Of particular interest as a sample source are mononuclear cells. As such, a preferred sample is one that is derived from peripheral blood mononuclear cells (PBMCs).

In these preferred embodiments in which the sample is a PBMC derived sample, the sample is generally a fluid PBMC derived sample. Any convenient methodology for producing a fluid PBMC sample may be employed. In many embodiments, the fluid PBMC derived sample is prepared by: (a) separating PBMCs from whole blood, i.e., collecting PBMCs, e.g., by centrifugation (such as by Ficoll-Hypaque density gradient centrifugation); (b) disrupting the collected cells, e.g., by contacting with a lysing buffer; (c) and removing the resultant cellular debris to obtain a cell-free extra, e.g., by centrifugation. A representative means for producing a suitable fluid PBMC derived sample, i.e, a fluid PBMC extract, is disclosed in WO 98/15646 and U.S. Pat. No. 5,985,565; the disclosures of which is herein incorporated by reference.

Once the patient derived sample is obtained, it is assayed for the presence or absence of one or more low molecular weight RNaseL fragments, either directly or indirectly. Specific low molecular weight RNaseL fragments of interest include, but are not limited to, those described above, including fragments 1, 2 and 3, where in many embodiments the fragments of interest are at least 1 and/or 3.

The sample may be assayed for the presence or absence of the low molecular weight RNaseL fragments using any convenient methodology. In many embodiments, such methodology involves the following two steps: (a) fractionation of the sample in a manner sufficient such that the one or more RNase L fragments and the native RNaseL (if present) are present in different fractions, i.e., separating the low molecular weight fragments from each other and from the native protein; and (b) detection of the low molecular weight fragments in the specific fractions, i.e., assaying each fraction for the presence or absence of an RNaseL fragment, where the detection may be qualitative, semi-quantitative or quantitative, and is usually at least semi-quantitative (i.e., not just qualitative).

In these embodiments, fractionation may be accomplished using any convenient methodology. The fractionation technique employed may or may not employ native or non-denaturing conditions. Whether fractionation is carried out under denaturing or non-denaturing conditions depends on the particular manner in which the low molecular weight fragments are detected, e.g. whether or not a non-denatured form is required for detection, where representative detection methods are described in greater detail below. Typically, the non-denaturing conditions are "native" conditions. By "native conditions" is meant fractionation by a process that substantially preserves the conformation and folding of the low molecular fragment species in the sample. Native conditions are those conditions that do not denature proteins. A variety of non-denaturing fractionation means are known to those of skill in the art, where one means of interest is gel filtration high performance liquid chromatography. Alternatively, fractionation may be carried out under nonnative, e.g., denaturing conditions, such as SDS-PAGE (sodium dodecylsulfate-polyacrylamide gel electrophoresis). As the fractionating step involves separating the various low molecular weight RNase L fragments, fractionation results in the production of one or more fractions that putatively contain the low molecular RNase L fragment (i.e. is suspected, of containing a low molecular weight fragment).

As discussed above, the sample or fraction(s) thereof are assayed for the presence or absence of low molecular weight RNaseL fragments, where the assay may be a direct assay or an indirect assay. By direct assay is meant an assay that provides for a direct detection of low molecular weight RNaseL fragments, e.g., an assay the yields direct information regarding the presence and often amount of low molecular weight RNaseL fragments in a sample, e.g., an assay where an RNase L specific antibody is employed to detect low molecular weight RNaseL fragments in an appropriately fractionated sample. By indirect assay is meant an assay that detects the presence or absence of low molecular weight RNaseL fragments through-detection, usually quantitation, of another species, e.g., native RNaseL and total RNaseL species (e.g., where a relative amount of native RNaseL to total RNaseL species in a sample is determined, from which the presence of low molecular weight RNaseL fragments is indirectly determined). An example of an indirect assay is the 2 5 A binding assay to detect native RNaseL and fragment 2 as described in the experimental section, infra, and based on Charachon et al. (1990), *Biochemistry* 29:2550–2556. As such, the assay employed may or may not also include a determination of the amount of native or full length RNaseL, i.e., RNaseL having a molecular weight of 80 kDa or higher, in the sample.

Any convenient assay protocol may be employed. Suitable assays that may be employed include antibody based assays, e.g., Western blot assays, such as those described in the experimental section infra. Antibody based assays require the use of antibodies specific for the RNaseL fragments and native RNaseL. The assays may be direct assays, i.e., those which employ antibodies specific for low molecular weight RNase L fragments. Alternatively, the assays may be indirect assays, i.e., those which detect native RNaseL and total amounts of RNase L species in a sample, e.g., an assay in which an antibodies specific for the C- and N-termini of the native RNase L are employed.

Antibodies that specifically bind to the subject RNaseL protein and low molecular weight fragments thereof can be prepared using a variety of convenient methods known to those of skill in the art. See Guide to Protein Purification, supra, as well as Antibodies, A Laboratory Manual (Harlow & Lane eds., Cold Spring Harbor Press)(1988). The antibodies may be polyclonal or monoclonal antibodies depending on the nature of the intended use, as long as they are specific for one or more forms of RNaseL or fragments thereof of interest, e.g., fragments 1, 2 or 3, as described above.

For preparation of polyclonal antibodies, the first step is immunization of the host animal with RNaseL or an immunogenic fragment, including fragment derivative thereof, where the RNaseL immunogen will preferably be in substantially pure form, comprising less than about 1% contaminant. The immunogen may comprise complete RNaseL or fragments or derivatives thereof. To increase the immune response of the host animal, the immunogen may be combined with an adjuvant, where suitable adjuvants include alum, dextran, sulfate, large polymeric anions, oil & water emulsions, e.g. Freund's adjuvant, Freund's complete adjuvant, and the like. The immunogen may also be conjugated to synthetic carrier proteins or synthetic antigens. A variety of hosts may be immunized to produce the polyclonal antibodies. Such hosts include rabbits, guinea pigs, rodents, e.g., mice, rats, sheep, goats, and the like. The immunogen is administered to the host, usually intradermally, with an initial dosage followed by one or more, usually at least two, additional booster dosages. Following immunization, the blood from the host is collected, followed by separation of the serum from the blood cells. The Ig present in the resultant antiserum may be further fractionated using known methods, such as ammonium salt fractionation, DEAE chromatography, and the like.

As with the preparation of polyclonal antibodies, the first step in preparing monoclonal antibodies specific for RNase L and fragments thereof is to immunize a suitable host, where suitable hosts include rats, hamsters, mice and the like, and are preferably mice. The immunogen, which as above, may be the entire protein or a fragment or derivative thereof, is administered to the host in any convenient manner, where such methods include: subcutaneous injection with adjuvants, nitrocellulose implants comprising the immunogen, intrasplenic injections, and the like, where the immunization protocol may be modulated to obtain a desired type of antibody, e.g. IgG or IgM, where such methods are known in the art. Following immunization, plasma cells are harvested from the immunized host, where sources of plasma cells include the spleen, lymph nodes and the like, with the spleen being preferred. The plasma cells are then immortalized with myeloma cells to produce hybridoma cells. A variety of myeloma cell lines are available and known to those of skill in the art. The plasma and myeloma cells are fused by combining the cells in a fusion medium usually in a ratio of about 10 plasma cells to 1 myeloma cell, where suitable fusion mediums include a fusion agent, e.g. PEG 1000, and the like. Following fusion, the fused cells are selected, e.g. by growing on HAT medium. Following hybridoma cell production, culture supernatant from individual hybridomas is screened for reactivity with RNase L using standard techniques, where such screening techniques include ELISA, dot blot immunoassays and the like. The antibody may be purified from the supernatants or ascites fluid by conventional techniques, e.g. affinity chromatography RNaseL bound to an insoluble support, protein A sepharose and the like.

The above prepared or obtained antibodies may be modified in a number of different ways to optimize their utility for use in a particular immunoassay. For example, antibody fragments, such as Fv, F(ab')$_2$ and Fab may be prepared by cleavage of the intact protein, e.g. by protease or chemical cleavage.

The antibodies, fragments or derivatives thereof may also be labeled in order to facilitate detection. A variety of protein labeling schemes are known in the art and may be employed, the particular scheme and label chosen being the one most convenient for the intended use of the antibody, e.g. immunoassay. Examples of labels include labels that permit both the direct and indirect measurement of the presence of the antibody. Examples of labels that permit direct measurement of the antibody include radiolabels, such as $^3$H or $^{125}$I, fluorescers, dyes, beads, chemilumninescers, colloidal particles, and the like. Examples of labels which permit indirect measurement of the presence of the antibody include enzymes where a substrate may provide for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that is conjugated to the enzyme, e.g. the antibody may be covalently bound to biotin and the enzyme conjugate to streptavidin. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In immunoassays of the subject invention, a number of different immunoassay formats are known in the art and may be employed. Representative assay formats include Western blots on protein gels or protein spots on filters, where the antibody is labeled as described above, as is known in the art.

Other immunoassays include those based on competitive formats, as are known in the art. One such format would be where a solid support is coated with RNase L. Labeled antibody is then combined with the patient derived sample suspected to produce a reaction mixture which, following sufficient incubation time for binding complexes to form, is contacted with the solid phase bound RNase L. The amount of labeled antibody which binds to the solid phase will be proportional to the amount of RNase L or fragments thereof in the sample, and the presence of RNase L and fragments thereof may therefore be detected. Other competitive formats that may be employed include those where the sample suspected of comprising RNase L fragments is combined with a known amount of labeled RNase L fragments and then contacted with a solid support coated with antibody specific for RNase L fragments. Such assay formats are known in the art and further described in both Guide to Protein Purification, supra, and Antibodies, A Laboratory Manual, supra. Sandwich-format assays may also be employed. A sandwich assay is performed by initially attaching a first of the two types of antibodies to an insoluble surface or support. This first antibody may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently. The insoluble supports may be any compositions to which antibodies or fragments thereof can be bound, which is readily separated from soluble material, and which is otherwise compatible with the overall method of measuring RNase L in the sample. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples. Before adding patient samples or fractions thereof, the non-specific binding sites on the insoluble support i.e. those not occupied by the first antibody, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used. Samples, fractions or aliquots thereof are then added to separately assayable supports (for example, separate wells of a microtiter plate) containing support-bound antigen. Preferably, a series of standards, containing known concentrations of RNAse L is assayed in parallel with the samples or aliquots thereof to serve as controls. Generally from about 0.001 to 1 ml of sample, diluted or otherwise, is sufficient, usually about 0.01 ml sufficing. Preferably, each sample and standard will be added to multiple wells so that mean values can be obtained for each. The incubation time should be sufficient for RNAse L molecules to bind the insoluble first antibody. Generally, from about 0.1 to 3 hr is sufficient, usually 1 hr sufficing. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample. After washing, a solution containing the second RNase L or RNase L fragment specific antibody is applied. The second antibody may be labeled, as described above, to facilitate direct, or indirect detection and/or quantification of binding. Examples of labels which permit direct measurement of immunocomplexes include radiolabels, such as $^3$H or $^{125}$I, fluorescers, dyes, beads, chemilumninescers, colloidal particles, and the like. Examples of labels which permit indirect measurement of binding include enzymes where the substrate may provide for a colored or fluorescent product. In a preferred embodiment, the second antibody is labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Alternatively, the antibody may be unlabeled. In this case, a labeled second receptor-specific compound is employed which binds to the second antibody. Such a second receptor-specific compound can be labeled in any of the above manners. It is possible to select such compounds such that multiple compounds bind each molecule of bound second receptor. Examples of second antibody/second receptor-specific molecule pairs include antibody/anti-antibody and avidin (or streptavidin)/biotin. Since the resultant signal is thus amplified, this technique may be advantageous where only a small amount of RNase L or fragment thereof is present. An example is the use of a labeled antibody specific to the second antibody. The volume, composition and concentration of second antibody solution provides for measurable binding to the RNase L already bound to the first antibody. Generally, the same volume as that of the sample is used: from about 0.001 to 1 ml is sufficient, usually about 0.1 ml sufficing. The concentration will generally be sufficient to saturate all RNase L potentially bound to first antibody. The concentration generally will be about 0.1 to 50 µg/ml, preferably about 1 µg/ml. The solution containing the second antibody is generally buffered in the range of about pH 6.5–9.5. The solution may also contain an innocuous protein as previously described. The incubation time should be sufficient for the labeled ligand to bind available molecules. Generally, from about 0.1 to 3 hr is sufficient, usually 1 hr sufficing. After the second antibody has bound, the insoluble support is generally again washed free of non-specifically bound second receptor, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and O-phenylenediamine which yields a colored product under appropriate reaction conditions. Appropriate substrates for,other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490–495 nm is conveniently measured with a spectrophotometer.

Depending on the particular nature of the antibody based assay employed, it may be desirable to employ antibodies that are capable of distinguishing between the various RNase L forms and fragments thereof. For example, in a Western blot assay a single type of antibody that recognizes all of the various RNase L fragments and the native RNase L itself may be employed, since the various fragments and native protein are pre-separated, e.g. by gel electrophoresis. However, where the various fragments and native protein are not separated prior to detection, e.g. in the competitive and sandwich assays described above, it is desirable to use a plurality of antibodies which are capable of specifically recognizing only a single RNase L species of interest, with substantially no cross-reactivity with other RNase L species or fragments that may be present in the sample.

In the subject methods, the sample or fractions thereof are at least assayed for the presence or absence of the low molecular RNase L fragments or species, and often times the native species as well, where the assay may be a direct assay for low molecular weight fragments or an indirect assay for low molecular weight fragments, as indicated above. In some embodiments, qualitative results are sufficient. Thus, one may be interested in identifying the presence or absence of the low molecular weight RNase L fragments as a marker for the chronic immune disease, e.g., in the diagnostic methods described above. Alternatively, one may be interested in making a qualitative determination of the ratio of the low molecular weight species to the native species. In many embodiments, the assays employed at least provide semi-quantitative detection of the various molecular weight RNase L species, and not just qualitative detection.

In assaying for low molecular weight RNase L fragments or species in the subject methods, one may look for: (a) the presence or absence of the low molecular weight fragments; (b) the pattern of the low molecular weight fragments and, optionally full length RNase L (where by pattern is meant the presence of each fragment and, optionally relative amount of each fragment); (c) the ratio of the amounts of the various low molecular weight species to each other and/or to the full length RNase L; and the like; (d) the relative amount of high molecular weight or native RNase L to all RNase L species in the sample; etc.

In many embodiments, based on the presence or absence of the various molecular weight RNase L species, and usually the semi-quantitative values obtained for each of the species of interest, the chronic immune disease activity in the subject from which the sample was derived is characterized. This broad category of embodiments includes those in which the low molecular weight RNase L species are directly assayed, e.g., those methods where: (a) the simple presence or absence of low molecular weight species is used to characterize the disease; (b) the ratio of low molecular weight species to high molecular weight species is used to characterize the disease; and (c) the pattern or amounts of two or more different low molecular weight species is used to characterize the disease; etc.

In yet other embodiments, e.g., those based on assays which indirectly determine the presence or absence of low molecular weight RNase L species, the relative amounts of the various RNase L species in the sample to each other, e.g., the relative amount of native or high molecular weight RNase L to the total amount of RNase L, i.e., native RNase L and fragment species thereof, in the sample is used to characterize the chronic immune disease activity in the subject. See e.g., the 2 5 A binding assay to detect native RNaseL and fragment 2 as described in the experimental section, infra Characterization of chronic immune disease activity according to the subject methods typically involves comparing the results obtained to a table or other source of predetermined values or reference values which provide information about the disease activity in the host, e.g., that positively or negatively correlate to the presence of the chronic immune disease, a particular stage of the chronic immune disease, and the like. For example, a table of values may be consulted in this step, where the table comprises representative values for the high and low molecular weight proteins as found in patients suffering from the chronic immune disease of interest. The values may be presented in numerical form, in picture form (e.g., as bands on a gel), and the like. By comparing the observed values with these reference values, e.g., by comparing a pattern of the RNase L species in the sample to a reference pattern or picture, characterization of the disease activity, e.g., confirmation of diagnosis, determination of disease state, etc., is readily made. In other embodiments, the ratio of two or more of the different species and/or full length RNase L is then compared to reference list of ratios to characterize the chronic immune disease activity.

As summarized above, the subject methods are methods of characterizing chronic immune disease activity in a host. The term characterizing is used broadly to refer to derivation of any type of information about the state of the chronic immune disease in the host. As such, the subject methods may be used to confirm an initial diagnosis of chronic immune disease, to determine the state of the disease in a patient known to have the chronic immune disease, to monitor the progression of the disease, to predict the occurrence of an attack, and the like. Where the subject invention is employed to confirm an initial diagnosis, a sample is obtained from a subject suspected of having the chronic immune disease (where the subject may be identified as described supra). For example, the sample is assayed for the presence of the high and low molecular weight RNase L species, a ratio of the two species is derived and then compared to reference values, where the reference values correlate given ratios to the presence or absence of the chronic immune disease.

The subject methods are also employed to determine the stage of the chronic immune disease in the subject. In other words, the subject chronic immune disease activity characterization methods may be employed to determine whether the patient is in a remission stage, a chronic stage etc. For example, the subject methods may be employed to determine whether an MS patient is in the relapsing-remitting stage or in the chronic progressive stage of the disease. To determine the stage of the disease, the observed values for the one or more RNase L species, and ratios where desired, in the assayed sample are compared to reference values which are correlated to a particular stage of chronic immune disease, e.g., remitting relapsing or chronic progressive stage of MS.

In yet other embodiments, characterization of disease activity yields information concerning the disease progression in the patient, e.g., whether disease progression has accelerated or slowed. For example, the initial characterization date, i.e., the amount of high and low molecular forms in the patient derived sample, could be employed as a baseline value to evaluate subsequent testings, e.g., at some time following the initial testing, e.g., 3 months. If the amount of low molecular weight form decreases in subsequent testing, this indicates that the disease is not progressing. Alternatively, if the amount of low molecular weight form increases, this indicates that the disease is progressing in severity.

The characterization data obtained from the subject methods may also be used to determine whether a particular therapeutic regimen is having positive affects with respect to the progression of the disease. For example, at various time periods during the course of treatment, the subject methods may be performed to obtain a reading of the amount of high and low molecular weight forms of the RNase L species of interest. If the amount of the low molecular weight marker is increasing, this indicates that the treatment regimen is not having the desired effect. Alternatively, if the amount of the low molecular weight marker is decreasing, this indicates that the treatment regimen is working.

In yet other embodiments, the characterization data obtained from the subject methods is used to predict when a chronic immune disease attack, e.g., MS attack, may occur. In this embodiment, the characterization data is compared to reference values, where some of the reference values correlate to the occurrence of an attack.

Depending on the particular test protocol, the subject methods may further include one or more additional assays associated with the chronic immune disease of interest. For example, one may couple the subject methods with assays that look for the presence of low molecular weight proteins that exhibit RNase L activity, the ratio of high to low molecular weight proteins that exhibit RNase L activity, etc., as described in U.S. Pat. No. 5, 985,565 and U.S. patent application Ser. No. 09/300,814, the disclosures of which are herein incorporated by reference; and the RNase L fragment based assays described in U.S. patent application Ser. No. 09/571,582, the disclosure of which is herein incorporated by reference. Other representative assays of interest include biochemical assays capable of identifying MS activity in the subject, e.g., assays which detect the presence of oligoclonal bands in cerebral spinal fluid (CSF). A variety of such assays are known to those of skill in the art and may be employed in the subject methods. See e.g. Mehta et al. (1988), Electrophoresis. 9(3):126–8; Mehta, et al. (1981), *J Clin Lab Immunol.* 6(1):17–22; Trbojevic-Cepe et al. (1989), *Neurologija* 38(1):11–21; Lasne et al. (1981), *J Neurochem.* 36(5): 18724; Mehta et al. (1986), *J Neurosci Methods.* 16(4):277–82.

Also provided by the subject invention are kits for use in carrying out the subject methods. The kits at least comprise reagents necessary for carrying out the RNase L species detection assays, where such kits may include: RNase L and/or RNase L fragments specific antibodies and/or immunoassay devices comprising the same; members of a signal producing system, such as antibodies, enzyme substrates, and the like; various buffers for use in carrying out the subject detection assays; and the like. The kits may further include one or more reagents necessary for preparation of the patient derived sample, such as heparin, Ficoll-Hypaque, lysing buffer, protease inhibitor, and the like, e.g. where the patient sample is PBMC derived, etc. In addition, the subject kits may further include one or more components employed in fractionation of the sample, such as an electrophoretic medium or precursors thereof, e.g., dried precursors of polacrylamide gels, one or more buffer mediums or components thereof, and the like. In most embodiments, the kits further include at least an information storage and presentation medium that contains reference data with which assay results may be compared in order to diagnose and/or characterize the, chronic immune disease activity in the subject being assayed, i.e., reference data that includes various values of the high and low molecular weight RNase L species and relates these values to the presence or absence of chronic immune disease and/or the activity of the disease in the host. The information storage and presentation medium may be in any convenient form, such as a printed information on a package insert, an electronic file present on an electronic storage medium, e.g., a magnetic disk, CD-ROM, and the like. In yet other embodiments, the kits may include alternative means for obtaining reference data, e.g. a website for obtaining the reference data "on-line." The kits may further include means for obtaining the patient sample, e.g., a syringe. The subject kits further typically include instructions for carrying out the subject methods, where these instructions may be present on a package insert and/or the packaging of the kit. Finally, the kit may further include one or more reagents from an additional biochemical assay which is used to detect the presence of and/or characterize the chronic immune disease of interest. For example, where MS is the chronic immune disease of interest, the kits may further include one or more reagents from an assay designed to detect the presence of oligoclonal bands in CSF, e.g., immunoxification reagents (e.g. anti-IgG); labeling reagents, such as silver, salts, and the like.

Treatment Methods

As summarized above, the subject invention also provides methods for treating a host suffering from a chronic immune disease. Specifically, the subject invention provides methods of treating a host suffering from MS or CFS.

In practicing the subject methods, an effective amount of an agent that enhances RNase L homodimer activity, particularly an agent that enhances RNase L homodimer apoptotic activity, specifically in PBMC, is administered to the host suffering from the chronic immune disease. By enhance is meant that the RNase L homodimer activity, particularly apoptotic activity, in the host, particularly in PBMC of the host, is increased by at least about 2 fold, usually by at least about 3 fold and more usually by at least about 5 fold, as compared to that observed in a control, i.e., a PBMC from the host that has not been contacted by the active agent(s).

Enhancement of RNase L homodimer activity can be accomplished in any convenient manner, where the mode of RNase L homodimer activity enhancement typically comprises administering an agent or agents that modulate one or more of the pathways depicted in FIG. 1. Particular active agents of interest include, but are not limited to: RNase L cleavage-inhibitory agents; RNase L expression enhancing agents; 2 5 A enhancing agents; and RNase L fragment antagonists. Each of these types of agents is now described separately in greater detail.

RNase L Cleavage-inhibitory Agents

RNase L cleavage-inhibitory agents of interest for use in the subject methods are agents that inhibit cleavage or fragmentation of RNase L. The target molecule is a protein or activity, e.g., enzyme, that cleaves native RNase L into fragments, e.g., fragments 1, 2 and/or 3, as described above. By inhibit is meant that these agents at least reduce, if not substantially or complete stop, the cleavage of RNase L.

RNase L cleavage-inhibitory agents typically reduce the cleavage or RNase L by at least about 2 fold, usually at least about 3 fold and more usually at least about 5 fold. Inhibitors of interest include agents that bind to the target molecule (e.g., protease) and concomitantly reduce its activity, as well as agents that reduce the expression of the target molecule so that the overall cleavage activity of the target molecule is reduced. As such, agents of interest include small molecule agents, as may be identified in the assays described below and antibodies specific to inhibiting the action of the RNase L cleaving target molecules. Small molecule agents of interest include small organic compounds having a molecular weight of more than 50 and less than about 2,500 daltons. The small molecule agents comprise functional groups necessary for structural interaction with proteins, particularly hydrogen bonding, and typically include at least an amine, carbonyl, hydroxyl or carboxyl group, preferably at least two of the functional chemical groups. The small molecule agents often comprise cyclical carbon or heterocyclic structures and/or aromatic or polyaromatic structures substituted with one or more of the above functional groups. Small molecule agents of interest are also found among biomolecules including, but not limited to: peptides, saccharides, fatty acids, steroids, purines, pyrimidines, derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modelling. Protease specific antibodies may be readily produced using the procedures described above.

In yet other embodiments of the invention, the active agent is an agent that modulates, and generally decreases or down regulates, the expression of the RNaseL-specific protease gene in the host. Antisense molecules can be used to down-regulate expression of genes in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur, phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural; β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozmes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43–56.

A further alternative to the above is the use of double-stranded RNA sequences, or the production thereof by introducing vectors for such in the host, the nucleic acid sequences of which are identical to all or part of the RNase L-specific protease gene. Such a double-stranded RNA is capable of binding to and causing the degradation of the homologous mRNA species. Thus, the mRNA coding for the production of RNase L-specific protease is targeted for removal by this method. This technique is referred to as RNA interference, examples of which are described in Tuschl et al. (1999), *Genes and Development* 13:3191–3197 and Zamore (2000), *Cell* 101:25–33.

RNase L Expression Enhancing Agents

In yet other embodiments of the subject invention, the active agent is an RNase L expression enhancing agent. By RNase L expression enhancing agent is meant an agent that enhances expression of native RNase L mRNA, the production of native RNase L protein, and/or the formation of cleavage-resistant homodimers of native RNaseL in the host, particularly in PBMC of the host. Agents of interest include, but are not limited to: RNase L nucleic acid and protein therapeutic compositions. In this embodiment, the genes or gene fragments are useful in gene therapy to enhance RNase L gene activity. Expression vectors may be used to introduce the RNase L gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g., plasmid; retrovirus, e.g. lentivirus; adenovirus; and the like, where the vectors are able to transiently or stably be maintained in the cells, usually for a period of at least about one day, more usually for a period of at least about several days to several weeks.

The gene or protein may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA and then bombarded into skin cells.

The nucleic acid and protein sequence of RNase L is known, where the human cDNA and amino acid sequence are deposited in GenBank under Accession no. L10381.

Also of interest is the use of agents that modulate the endogenous RNase L gene of the host to enhance its expression. For example, the endogenous RNase L gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the enhancement of RNase L expression without manipulation of the encoding nucleic acid itself, but instead through integration of a regulatory sequence into the genome of cell of the host that already includes a gene encoding the desired protein, as described in the above incorporated patent documents.

2 5 A Enhancing Agents

Also of interest in certain embodiments are 2 5 A enhancing agents. By 2 5 A enhancing agents is meant agents that increase the amount of 2 5 A that is able to bind to and activate RNaseL in the host, and particularly PBMC of the host, and thereby increase the amount of RNase L homodimer in the host. By increasing the amount of 2 5 A in the host is meant an agent that increases the amount of bioactive 2 5 A in the host, as compared to a control, by at least about 2 fold, usually by at least about 3 fold and more usually by at least about 5 fold. The agent may increase the amount of bioactive 2.5 A in the host, particularly in PBMC of the host, in a number of different ways. For example, the agent may increase the expression and/or activity of 2 5 A synthetase (the p40/46 and p69/71 isoforms), where such agents are analogous to those described above for enhancing RNase L expression. The agent may also be a nucleic acid agent, e.g., a dsRNA agent, such as those described in WO 91/00097, the disclosure of which is herein incorporated by reference. Where such agents are employed, they are equally employed in combination with a diagnostic step, as described above, e.g., an assay for the presence of fragments 1, 2, and/or 3.

RNase L Fragment Antagonists

Also of interest in many embodiments are agents that are RNase L fragment antagonists. By RNase L fragment antogonist is meant an agent that inhibits the activity of an RNase L fragment, e.g., the NF-κB like activity of RNase L fragment 1; the Cdk6 like anti-apoptotic activity of fragment 3, etc. In other words, an RNase L fragment antagonist is an agent that inhibits RNase L fragment anti-apoptotic activity. Agents of interest include, but are not limited to: agents that specifically bind to the RNase L fragments and, in doing so, prevent or inhibit their interaction with their cellular target that gives rise to the anti-apoptotic activity. Agents of interest include small molecule agents, such as those described above, and RNase L fragment specific antibodies, which antibodies can be prepared according to the methods described above.

As mentioned above, in the subject methods an effective amount of one or more of the above described active agents is administered to the host, where "effective amount" means a dosage sufficient to produce a desired result, where the desired result is at least an amelioration, if not complete cessation of the chronic immune disease symptoms.

In the subject methods, the active agent(s) may be administered to the host using any convenient means capable of resulting in the desired treatment. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may: also be used for intramuscular administration, as described by Furth et al (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

As mentioned above, by treatment is meant that at least an amelioration of the symptoms associated with the chronic immune disease, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the chronic immune disease condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest Preferred compounds and unit doses are those described herein above.

Screening Methods

As mentioned above, also provided by the subject invention are screening methods for evaluating the RNase L cleavage-inhibitory activity of a candidate agent and screening methods for evaluating the RNase L fragment antagonist activity of a candidate agent. As such, the subject invention provides methods for screening one or more, including collections or libraries of, agents for RNase L cleavage-inhibitory activity. In these assay methods of the subject invention, a candidate agent (or agents) is contacted with a source of: RNase L protease, e.g., a subject sample, as described above, and a source of native RNase L under conditions sufficient for RNAse L protein cleavage products to be generated. Generally, contact is maintained for a period of time sufficient for cleavage to occur, where this incubation time typically ranges from about 5 to 120 minutes, usually from about 30 to 60 minutes. The source of RNase L may be used in these assays may be any convenient source. As such, the source may be a naturally occurring source, a recombinant source and the like. Following the incubation period, the resultant reaction mixture is assayed for the presence and/or amount of RNase L fragments, e.g., fragments 1, 2 and/or 3. The assay protocols described above may be employed.

As such, any convenient cleavage product detection format may be employed. Depending on the detection format employed, the source of RNase L may or may not be labeled. For example, one convenient assay employs the use of substrate bound RNase L, where the proteins are labeled, generally proximal to or at the end of the protein that is not attached, either directly or indirectly, to the substrate. The substrate bound protein is then contacted with the sample, as described above, and, following incubation, any cleavage products, e.g. low molecular weight RNAse L cleavage products, are detected. Non-labeled protocols may also be employed, e.g. antibody based (such as Western blot formats) as described supra.

Following detection of the cleavage products, the presence of, and generally amount of, cleavage products is related to the RNase L cleavage-inhibitory activity of the candidate agent. In other words, the results of this assay procedure are then related to the RNase L cleavage-inhibitory activity of the test compound, typically through comparison to a control. In other words, the inhibitory activity of the test compound is deduced or extrapolated, i.e., derived, from the assay results.

Also provided are cell based assays for evaluating the RNase L fragment antagonist activity of a candidate agent or agents. In these methods, a cell comprising RNase L fragments, e.g., a PBMC derived from a chronic immune disease suffering patient, such as a CFS or MS patient, is contacted with the candidate agent under conditions sufficient for the candidate agent to be internalized by the cell. The result of the candidate agent on the cell phenotype, specifically on whether the cell progresses to apoptosis, is then evaluated. Any convenient method of evaluating cellular apoptosis may be employed, where suitable methods include, but are not limited to the measurement of: 1) the expression of genes related to the apoptotic cycle (i.e., caspases, specific cytokines), 2) the production of proteins related to the apoptitic cycle (e.g., caspases, specific cytokines), or 3) the fragmentation of cellular DNA as measured by flow cytometry or agarose gel electrophoresis. The results of the apoptosis assay are then employed to evaluate or deduce the RNase L fragment antagonist activity of the candidate agent.

In the above assays, a variety of different candidate agents may be screened for relevant activity. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modelling.

Also provided are kits for use in practicing the subject screening methods. The subject kits include, among other components, a source of RNase L (e.g., source of fill length RNase L), where the source may be stably associated with the surface of a substrate and/or labeled, depending on the nature of the assay to be performed. Generally, the kits will also comprise a medium having reference values recorded thereon for use in interpreting the assay data and relating the data to the proteolytic activity in the sample. Depending on the nature of the assay to be performed, the kit may also include cells or cell lines known to include RNase L fragments; a source of protease specific for RNase L, etc.

The following examples are offered by way of illustration and not by way of limitation.

EXPERIMENTAL

Experimental Section

I. Analysis and Quantification of RNase L Protein and Related Fragments in Cell Extracts from Healthy Controls, CFS Patients, and CFS Patients Undergoing Therapy with Mismatched Double-stranded RNA Study subjects were four patients (Patients A, B, C, and D) who had been previously diagnosed as fulfilling the diagnostic criteria for CFS per the Centers for Disease Control and Prevention (CDC) guidelines of 1988 (Holmes et al. (1988), *Ann. Intern. Med.* 108:387–389, 1988), and who had been administered therapy with mismatched double stranded RNA for a period of at least six months. Levels of fatigue was assessed using the Karnofsky Performance Score (KPS) criteria Four healthy controls were included in the analysis. In addition, 44 patients previously diagnosed as fulfilling the diagnostic criteria for CFS, but not undergoing treatment with mismatched double stranded RNA, were evaluated for RNase L fragmentation and caspase levels.

All patients and controls were selected from a medical practice in Brussels, Belgium. At the time of blood sampling, patient symptoms were evaluated and recorded.

A. Procedures

1. Extraction

Peripheral blood mononuclear cells (PBMCs) were separated from heparinized blood (30 mLs) by Ficoll-Hypaque density gradient centrifugation. The blood was layered onto 20 mLs of Ficoll-Hypaque (Boyum, Scandinavian Journal of Clinical Laboratory Investigation, 97:101–109, 1968) at a density of 1.077 g/mL at 20° C. and centrifuged for 30 minutes at 500×g. The PBMC layer was removed and washed once with 5 volumes of phosphate buffered saline (PBS). The cells were then resuspended in 5 mLs of red blood cell lysing buffer (155 mM $NH_4Cl$, 10 mM $NaHCO_3$, 0.1 mM EDTA, pH 7.4), kept on ice for 5 minutes, then centrifuged for 5 minutes at 500×g. The resultant cell pellet was washed once with 15 mLs of PBS and centrifuged for 5 minutes at 500×g. The resultant pellet was then stored at −70 C until the protein extraction procedure could be performed.

To extract the proteins from the cell pellet, PBMCs were resuspended in a volume approximately 5–10 times the packed cell volume in the extract buffer (10 mM HEPES, pH 7.6, 90 mM KCl, 1.5 mM $Mg(OAc)_2$, 10.5% non-ionic detergent (such as Nonidet P40 or Igepal CA-630, Sigma Chemical Corporation)). The extract buffer also contained a mixture of protease inhibitors to help stabilize the extract and impeded the action of proteases. One such commercially available mixture is the MiniComplete protease inhibitor cocktail (Boehringer-Mannheim) containing aprotinin, leupeptin, pefabloc-SC and EDTA.

The extraction procedure was performed at 24 degrees C., holding the cell pellet-extraction buffer in ice water or on wet ice for 5 minutes. The cell pellet-buffer mix was then vortexed at medium speed for 2 minutes at room temperature to ensure complete solubilization of the cell membranes. The cell pellet-buffer mix was then placed at 2–4 C for an additional 5 minutes. The final step was to centrifuge the cell pellet-buffer mix at high speed in a microcentrifuge (16,000×g) for 2 minutes. The supernatant containing the proteins of interest was collected and the cell pellet was discarded. All cell extracts were stored at −70 C until further analysis could be performed.

Quantification of protein in the patient cell extracts was performed using a standard commercially available procedure of a modified Bradford method (Bio-Rad Laboratories) following the manufacturer's recommended procedure.

2. Quantification of 2 5 A Binding Proteins

Analysis of LMW and HMW RNase L Proteins was performed using a radiolabeled 2 5 A trimer and SDS-PAGE as described by the method of Charachon et al. (1990), *Biochemistry* 29:2550–2556. Briefly, 2 5 A trimer was radiolabeled by the ligation of $^{32}$P-pCp to the 3' end (method of Charachon). After removal of the 3' terminal phosphate by treatment with bacterial alkaline phosphatase, the 3' ribose residue of pC was oxidized with sodium metaperiodate (10 mM final concentration, pH 4.75) for one hour at 4 C to form 2 5 A-$^{32}$pC-OX. This reaction mixture was subsequently equilibrated to pH 8.0 by the addition of NaOH. This oxidized molecule was used as the radiolabel in all subsequent reactions for RNase L protein analysis (referred to below as radiolabeled 2 5 A).

The radiolabeled 2 5 A was incubated with 200 micrograms of cell extract at 2–4 C for 15 minutes to allow the radiolabeled 2 5 A to interact with any 2 5 A -binding proteins.; present, such as RNase L (all molecular weight species). The 2 5 A radiolabel was then covalently attached to all RNase L species by the addition of cyanoborohydride (20 mM in 100 mM phosphate buffer, pH 8.0). The reduction reaction was allowed to occur for 20 minutes at room temperature. SDS-PAGE sample buffer, including a tracking dye, was added to the samples and all samples were incubated at 95 C for 5 minutes under reducing conditions.

The samples were then subjected to standard SDS-polyacrylamide gel electrophoresis using a 4 percent stacking gel and a 10 percent separating gel (Bisbal et al. (1989), *European Journal of Biochemistry* 179:595–602). Also included in the first lane of each gel was a molecular weight marker, pre-stained to be visible as it migrated during the course of electrophoresis (Bio-Rad Laboratories). The gel was electrophoresed until the tracking dye had migrated to the bottom of the gel. (approximately 5 hours at a constant current of 30 mAmps). The gel was then dried and subjected to autoradiography (Bio-Rad Laboratories FX Imager).

The autoradiographs were then analyzed by densitometry, and quantification of any and all RNase L species present was performed using specialized software (Quantity One from Bio-Rad Laboratories). The results are expressed as the density (or relative amount) of 37 kDa LMW RNase L present divided by the density (or relative amount) of 80 kDa HMW RNase L present, multiplied by a constant factor of 10.

3. Quantification of RNase L Protein and Related Fragments by Western Blot

Briefly, the procedure used was as follows: 200 micrograms of protein extracted from the cytoplasm of PBMCs was mixed with 2×SDS-PAGE gel sample dye that included a tracking dye, and heated to 95 C for five minutes to denature the proteins. The denatured samples were then subjected to standard SDS-PAGE using a 4 percent stacking gel and 10 percent separating gel. Also included in the first lane of each gel was a molecular weight marker, pre-stained to be visible as it migrated during the course of electrophoresis (Bio-Rad Laboratories). The gel was electrophoresed until the tracking dye had migrated to the bottom of the gel.

The gel was then transferred to a PVDF membrane (Bio-Rad Laboratories) using a semi-dry transfer system (Amersham-Pharmacia Biotech). Transfer was performed at an average current of 0.8 milliamp per cm$^2$ of gel (or 100 mA for a standard 15 cm×8 cm gel) for two hours. After transfer was complete (as determined by the visual agreement of the transfer of the color from the pre-stained molecular weight markers to the membrane), the membrane was allowed to dry thoroughly at room temperature for at least one hour.

Western blotting was performed using the following format: The membrane was first wet with a minimum volume of 100 percent methanol (according to the manufacturer's instruction). Then a solution of five percent non-fat dry milk (5% NFDM) was used to 'block' the membrane ('blocking buffer') to eliminate non-specific background binding of antibody. The membrane was 'blocked' for one hour with gentle shaking on an orbital shaker.

The blocking buffer was discarded and fresh blocking buffer was added in the amount of approximately 0.1 mL per cm$^2$ of membrane, to which was added the primary antibody (rabbit anti-RNase L) at a 1:100 dilution. The membrane was allowed to react with the primary antibody for one hour with gentle shaking on an orbital shaker. The primary antibody solution was then discarded and the membrane was washed three times with 25 mLs per wash of phosphate buffered saline (PBS, pH=7.4) plus 0.1% Tween 20 (polyoxyethylene sorbitan monolaurate; Sigma Corporation). Each wash was five minutes in length, with shaking, and the each time the solution was discarded.

Fresh blocking buffer was added in the amount of approximately 0.1 mL per cm$^2$ of membrane, to which was added the secondary antibody (goat anti-rabbit antibody, conjugated to horseradish peroxidase (GAR-HRP); Bio-Rad Laboratories) at a 1:2000 dilution according to the manufacturer's recommendations. The membrane was allowed to react with the secondary antibody for thirty minutes with gentle shaking on an orbital shaker. The secondary antibody solution was discarded and the membrane was washed three times with 25 mLs per wash of phosphate buffered saline (PBS, pH=7.4) plus 0.1% Tween 20. Each wash was five minutes in length, with shaking, and the each time the solution was discarded.

Color development was performed using the Opti4-CN kit (Bio-Rad Laboratories) according to the manufacturer's recommendations. Color development was allowed to proceed for 15 minutes and the membrane was then rinsed in copious changes of water and allowed to dry at room temperature. The membrane was then analyzed by densitometry and quantification of RNase L and RNase L fragment proteins present was performed using specialized software (Quantity One from Bio-Rad Laboratories).

4. Measurement of Caspase Levels in PBMC Extracts

Caspase levels in PBMC extracts were measured using a commercially available kit (BioSource International) based on a calorimetric assay. Briefly, PBMC extracts were diluted to a final concentration of 1 microgram of protein per 50 microliters of diluent (provided with the kit). This sample (1 microgram) was then added to 55 microliters of assay buffer containing a substrate specific for the particular caspase to be measured (if caspase activity is present, the substrate is cleaved, liberating color).

Cell extracts to be used as positive and negative controls for caspase activity levels were prepared using the method of Mashima et al. (1999), *Oncogene* 14:1007–1012. Briefly, the human monocytic leukemia cell line U937 was induced to begin apoptosis by treatment with camptothecin at a concentration of 10 micrograms per mL of $2 \times 10^6$ cells. Uninduced cells were used as the negative control. Also included as a negative control were normal human monocytes, elutriated and frozen as live cells. All cell extracts and protein determinations were made as described above.

The reaction mixture (1 microgram protein sample+ caspase substrate) was incubated at 37 degrees C. for 20–24 hours. The resultant color was measured using a spectrophotometer at a wavelength of 405 nm. Background absorbance (i.e., from a reagent blank without protein) was subtracted from all sample values. All assays were performed in triplicate, B. Analysis of Results 1. Tabular Results

TABLE #1

Caspase and RNase L Measurements of PBMC Specimens from CFS Patients - Analysis of Variance and Level of Significance

| I.D. | | n | C2 | C3 | C6 | C8 | C9 |
|---|---|---|---|---|---|---|---|
| Monocytes (G1) | | 3 | 52 ± 12 | 77 ± 1 | 75 ± 3 | 63 ± 10 | 28 ± 5 |
| Cell Line Uninduced (G2) | | 4 | 50 ± 32 | 73 ± 26 | 162 ± 20 | 91 ± 11 | 45 ± 6 |
| Cell Line Induced (G3) | | 4 | 251 ± 39 | 304 ± 50 | 277 ± 57 | 207 ± 52 | 90 ± 29 |
| RNase L Ratio | | | | | | | |
| 0–2 | (P1) | 12 | 77 ± 48 | 105 ± 51 | 103 ± 40 | 81 ± 32 | 39 ± 10 |
| 2–4 | (P2) | 3 | 65 ± 42 | 113 ± 53 | 98 ± 24 | 100 ± 18 | 33 ± 7 |
| 4–6 | (P3) | 6 | 50 ± 27 | 99 ± 54 | 102 ± 43 | 90 ± 38 | 35 ± 10 |
| 6–8 | (P4) | 6 | 111 ± 67 | 263 ± 146 | 199 ± 98 | 192 ± 79 | 59 ± 28 |
| 8–10 | (P5) | 6 | 68 ± 51 | 207 ± 117 | 142 ± 66 | 123 ± 49 | 40 ± 16 |
| 10–20 | (P6) | 6 | 44 ± 25 | 148 ± 69 | 116 ± 33 | 103 ± 30 | 36 ± 10 |
| >20 | (P7) | 5 | 20 ± 10 | 66 ± 19 | 141 ± 24 | 77 ± 31 | 20 ± 10 |
| ANOVA Analysis (p-value) | | | | | | | |
| P4 vs. G3 | | | <0.001 | NS | <0.05 | NS | <0.05 |
| P5 vs. G3 | | | <0.001 | NS | <0.01 | <0.05 | <0.001 |
| G2 vs. G3 | | | <0.001 | <0.01 | <0.05 | <0.01 | <0.01 |
| G1 vs. G3 | | | <0.01 | <0.05 | <0.01 | <0.01 | <0.01 |
| P4 vs. G1 | | | NS | <0.01 | <0.05 | <0.01 | <0.05 |
| P4 vs. G2 | | | NS | <0.01 | NS | <0.01 | NS |
| P4 vs. P1 | | | NS | <0.001 | <0.01 | <0.001 | <0.05 |
| P4 vs. P2 | | | NS | <0.05 | <0.05 | <0.05 | <0.05 |
| P4 vs. P3 | | | <0.05 | <0.01 | <0.01 | <0.01 | <0.05 |
| P4 vs. P5 | | | NS | NS | NS | <0.05 | NS |
| P4 vs. P6 | | | <0.05 | <0.05 | <0.05 | <0.01 | <0.05 |
| P4 vs. P7 | | | <0.01 | <0.01 | NS | <0.01 | <0.01 |
| P5 vs. G1 | | | NS | <0.05 | NS | NS | NS |
| P5 vs. G2 | | | NS | <0.05 | NS | NS | NS |
| P5 vs. P1 | | | NS | <0.05 | NS | NS | NS |
| P5 vs. P2 | | | NS | NS | NS | NS | NS |
| P5 vs. P3 | | | NS | <0.05 | NS | NS | NS |
| P5 vs. P6 | | | NS | <0.05 | NS | NS | NS |
| P5 vs. P7 | | | NS | <0.05 | NS | NS | NS |
| P1 vs. P7 | | | <0.05 | NS | NS | NS | <0.05 |
| G2 vs. P7 | | | NS | NS | NS | NS | <0.05 |

TABLE #2

Caspase 3 Analysis of Specimens from CFS Patients in the Course of Treatment With Mismatched dsRNA

| | Caspase 3 Activity mAU ± s.d. of triplicates | | | | | |
|---|---|---|---|---|---|---|
| I.D. | Before Therapy | p vs. G3 | After Therapy | p vs. G1 | After Relapse | p vs. G1 |
| Healthy Controls (G1) | 140 ± 28 | <0.001 | | | | |
| Cell Line Uninduced (G2) | 82 ± 9 | <0.001 | | | | |
| Cell Line Induced (G3) | 336 ± 6 | | | | | |

TABLE #2-continued

Caspase 3 Analysis of Specimens from CFS Patients in the Course of Treatment With Mismatched dsRNA

| Patient A | 125 ± 12 | <0.05 | 125 ± 16 | NS    |        |        |
|-----------|----------|-------|----------|-------|--------|--------|
| Patient B | 264 ± 14 | NS    | 81 ± 12  | <0.05 |        |        |
| Patient C | 68 ± 18  | <0.01 | 59 ± 13  | <0.01 |        |        |
| Patient D | 270 ± 9  | NS    | 100 ± 10 | NS    | 41 ± 3 | <0.001 |

| I.D. | RNase L ratio Before Therapy | KPS | RNase L ratio After Therapy | KPS | RNase L ratio After Relapse | KPS |
|------|------|-----|------|-----|------|-----|
| Patient A | 17.6 | 60 | 0.6  | 80 | n/a  |    |
| Patient B | 10.1 | 60 | 0.3  | 90 | n/a  |    |
| Patient C | 2.9  | 70 | 31.0 | 60 | n/a  |    |
| Patient D | 8.7  | 60 | 0.6  | 80 | 52.9 | 60 |

2. Discussion

FIG. 1 represents a diagram of the role of native RNase L protein in the normal antiviral and apoptotic response pathways within the host. The induction of native RNase L, when accompanied by an increase in production of 2 5 A trimer or tetramer, causes the subsequent formation of RNase L homodimers that play an active role in the selective degradation of viral RNA. In addition, RNase L homodimers have been demonstrated to stimulate apoptosis, leading to death of the infected and/or damaged cell.

The lower molecular weight fragments of RNase L are produced from the specific cleavage of native RNase L by a protease(s). These fragments then play a selective role in inhibiting the apoptotic pathway, in effect keeping the damaged cell alive and the immune system dysfunctional.

Figures 2, 2A, 2B, 2C:
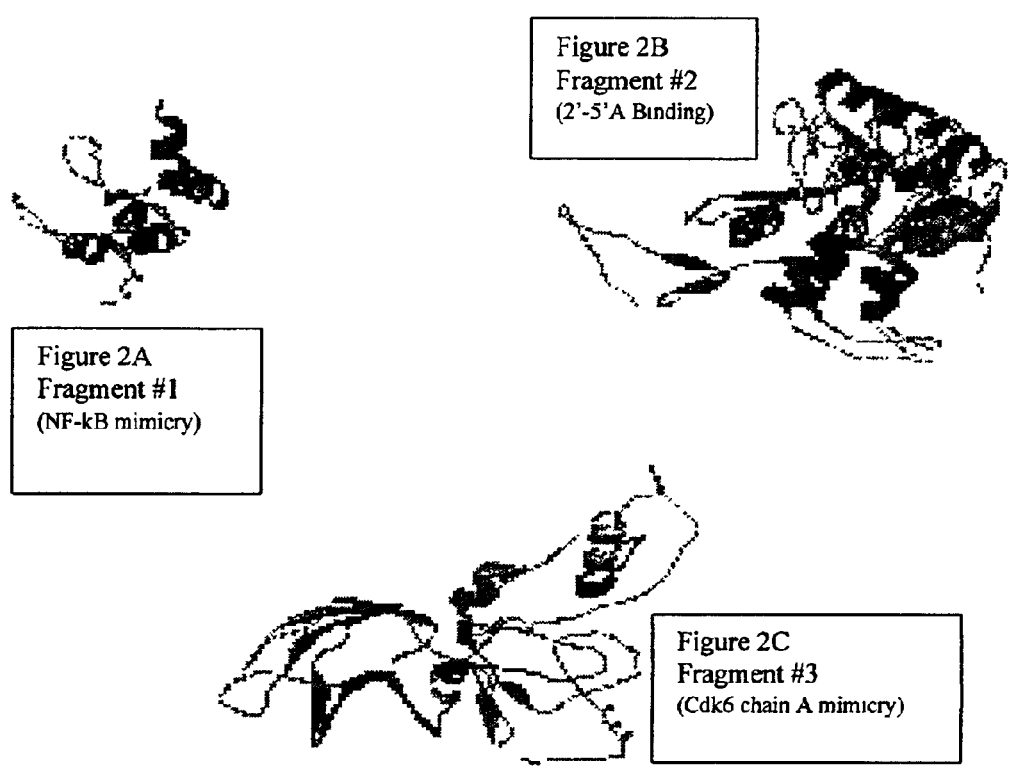
FIGS. 2A to 2C provide three-dimensional representations of RNase L fragments 1 to 3, respectively.

FIGS. 2A to 2C represent three dimensional views of three different fragments generated upon cleavage of native RNase L by various proteases. Fragment #1 contains the ankyrin binding repeat domain and thus can interact with various membrane transport proteins. In addition, this fragment has a 47 percent amino acid sequence homology with NF-kB. NF-kB has been demonstrated to induce transcriptional activities within a cell to promote cell growth (thus acting in an anti-apoptotic fashion).

Fragment #2 is the 2 5 A binding fragment that also has catalytic activity (i.e., can degrade RNA). However, as it has lost the 'dimerization' region, it needs only to bind 2 5 A to be active. In addition, this fragment competes with the native RNase L protein for free 2 5 A, reducing the chances for native homodimerization to occur, and inhibiting the complete induction of apoptosis.

Fragment #3 shares a 45 percent amino acid homology with chain A of the cyclin-dependent kinase Cdk6 that acts to block apoptosis by driving G1 progression during the cell cycle.

Figure 3:
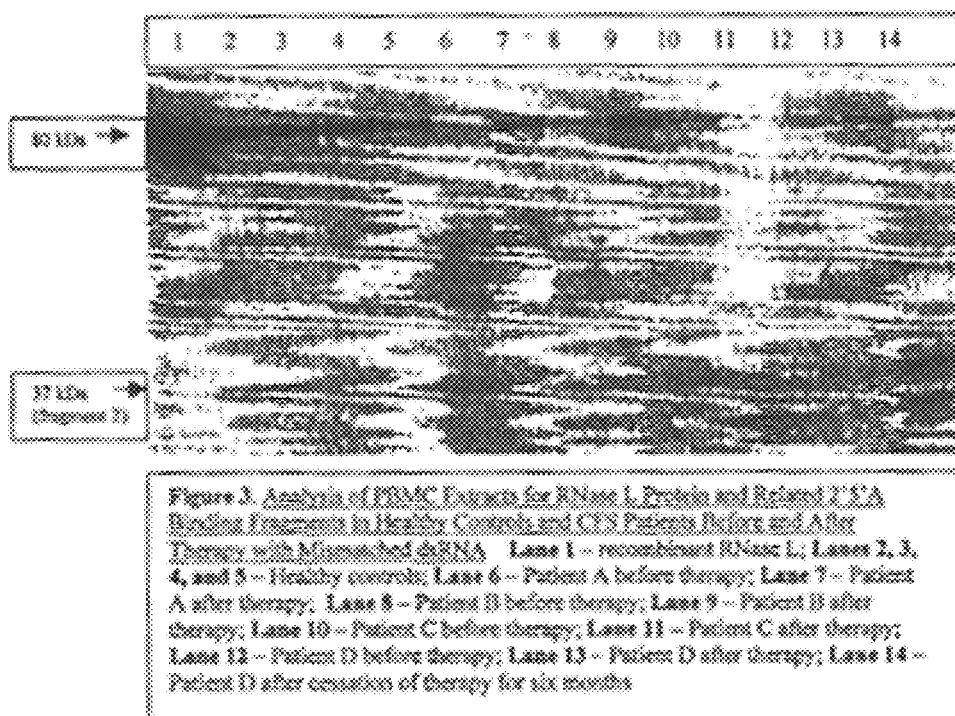
FIG. 3 provides an analysis of PBMC extracts for RNase L protein and related 2 5 A binding fragments in healthy controls and CFS patients before and after therapy with mismatched dsRNA.

In FIGS. 3 and 4, and in Table 2 below, the exact same clinical specimen was used from the same four patients (i.e., Patients A, B, C, and D) before and after therapy with mismatched double-stranded RNA.

FIG. 3 represents a densitometric scan of RNase L and other 2 5 A -binding proteins detected in PBMC extracts from CFS patients before and after treatment with mismatched double-stranded RNA. The native RNase L is clearly visible at 80 kDa (upper left arrow).

One low molecular weight fragment at 37 kDa (specifically observed in CFS patients before therapy and after relapse) is indicated (lower left arrow). The following results are noted:

In Lanes 2–5, the Healthy Controls have a strong 2 5 A -binding band at 80 kDa, representing native RNase L In Lane 6, Patient A has less native 80 kDa before therapy, and more following therapy (Lane 7)

In Lane 8, Patient B has less native 80 kDa before therapy, and more following therapy (Lane 9)

In Lane 10, Patient C has less native 80 kDa before therapy, but even less after therapy. This patient did not respond to treatment as evidenced by KPS evaluation (see Table 2)

In Lane 12, Patient D has less native 80 kDa before therapy, and more following therapy (Lane 13). The patient then relapsed, as evidenced by KPS evaluation. Upon assaying for RNase L, a severe decrease in the amount of native 80 kDa can be detected FIG. 4 represents a densitometric scan of a Western blot detecting native RNase L and related protein fragments in PBMC extracts from CFS patients before and after treatment with mismatched double-stranded RNA. The native RNase L is clearly visible at 8.0 kDa (left arrow). Fragments of RNase L (specifically observed in CFS patients before therapy and after relapse) are indicated by arrows on the right. As in FIG. 3, the exact same results may be noted regarding the presence, absence, and reappearance of the native 80 kDa RNase L in comparison to the other RNase L-related fragments.

In the data set forth in Table 1, the numerical average±standard deviation of the analysis in triplicate of caspase activity in PBMC extracts is provided. In the far left column, the identification (or I.D.) of the specimen is listed In this column, monocyte control extracts and uninduced and induced cell line extracts are listed first, as groups beginning with the letter 'G.' Next, CFS patient samples are listed as groups beginning with the letter 'P.' The 44 patients included in this analysis did not include the four patients used for the collection of data in FIGS. 3, 4, or Table 2.

The 44 patients were grouped according to their 'RNase L' ratio, calculated as "the ratio of the low molecular weight 2 5 A -binding species to high molecular weight (i.e., native) 2 5 A -binding species of RNase L , multiplied by a constant factor of 10." (Data not shown)

In the next column, 'n' represents the number of different specimens that were included in the groupings.

In each successive column, data are provided concerning the amount of caspase activity (caspases types 2, 3, 6, 8, and 9, represented as C2, C3, C6, C8, and C9) in the PBMC extracts.

Below the raw data are the analysis of variance, one way (or ANOVA), and the corresponding p-value, representing significance.

As one example derived from the results set forth in Table 1, it is evident that CFS patient group 4 (P4) has significantly elevated levels of caspase 3, 6, and 8 activities when compared to the other patient groups and the control monocytes and uninduced cell line. Indeed, the level of caspases in this group is statistically equal to the levels of caspases found in cells induced to undergo apoptosis with the synthetic chemical camptothecin.

Upon further analysis, it is evident that levels of all caspases assayed (C2, C3, C6, C8, and C9) at first increase, then decrease relative to the RNase L ratio in CFS patient groups P1 through P7, indicating that the apoptotic process is being inhibited when the levels of RNase L-related fragments reaches a certain point.

In the data set forth in Table 2, the numerical average±standard deviation of the analysis in triplicate of caspase 3 (C3) activity in PBMC extracts is provided. In the far left column, the identification (or I.D.) of the specimen is listed. In this column, healthy control extracts and uninduced and induced cell line extracts are listed first, as groups beginning with the letter 'G.' Data from analysis of the four CFS patients (Patients A, B, C, and D) then follows.

In the successive columns entitled 'Before Therapy' (i.e., at baseline), 'After Therapy,' and 'After Relapse,' caspase 3 activity is provided along with an analysis of variance, one way. (or ANOVA), and the corresponding p-value, representing significance. The 'therapy' is mismatched double-stranded RNA administered as previously described (Strayer, et al. (1994), *Clin. Infect. Dis.*, 18 (Suppl.1) :S88–95).

Below the caspase 3 data are the RNase L ratios of the same group of CFS Patients (Patients A, B, C, and D), measured using the same PBMC extracts as were used in for the caspase activity determinations. The 'RNase L' ratio is calculated as "the ratio of the low molecular weight 2 5 A -binding species to high molecular weight (i.e., native) 2 5 A -binding species of RNase L, multiplied by a constant factor of 10." Also included in this portion of the data are the Karnofsky Performance Scores (KPS) taken at the time of specimen collection.

From the results set forth in Table 2, a number of observations are noted, and are best detailed on a patient-by-patient basis.

Patient A responded to therapy, as can be determined by the increase in KPS (indicating an enhanced state of well-being) and concomitant decrease in RNase L ratio (see also FIGS. 3 and 4, Lanes 6 and 7). This patient's C3 levels did not vary before or after treatment and are in keeping with the data in Table #1 (as this patient would have been grouped in patient group 'P6').

Patient B responded to therapy, as can be determined by the increase in KPS and concomitant decrease in RNase L ratio (see also FIGS. 3 and 4, Lanes 8 and 9). This patient also had statistically significant increased levels of caspase 3 before therapy that returned to non-elevated levels after therapy.

Patient C did not respond to therapy, as can be determined by the decrease in KPS and concomitant increase in RNase L ratio (see also FIGS. 3 and 4, Lanes 10 and 11).This patient's caspase 3 levels were also statistically lower than controls, indicating that this patient may have had another disease in addition to CFS.

Patient D responded to therapy, as can be determined by the increase in KPS and concomitant decrease in RNase L ratio (see also FIGS. 3 and 4, Lanes 12 and 13).This patient also had statistically significant increased levels of caspase 3 before therapy that returned to non-elevated levels after therapy. However, six months after cessation of therapy the patient suffered a relapse, as was first documented by a decrease in KPS. Caspase 3 and RNase L ratio analyses demonstrated a statistically significant decrease in caspase 3 levels, with an elevated RNase L ratio (see also FIGS. 3 and 4, Lane 14), again in keeping with the data in Table #1, patient group P7, indicating a block in the apoptotic pathway in this patient's PBMCs.

From the above the following conclusions are made:

Increases or decreases in the relative amounts (i.e., ratios) of native RNase L when measured against RNase L-related fragments correlates strongly with the presence or absence of CFS disease, respectively Increases in apoptosis in PBMCs from CFS patients can be measured by analyzing caspase levels Increases in apoptosis in PBMCs from CFS patients can be measured by analyzing the relative amount of native RNase L and related fragments As the ratio of RNase L -related fragments to the remaining native RNase L protein increases above a certain level, the process of apoptosis, as measured by caspase levels, appears to stop then decline even further to sub-normal levels RNase L-related fragments are likely to inhibit the apoptotic process based on the amino acid sequence comparison of RNase L-related fragments to known inducers of cell activation and growth Upon successful therapy with mismatched double stranded RNA, RNase L ratios return to 'normal' or healthy control levels Upon successful therapy with mismatched double stranded RNA, caspase levels return to 'normal' or healthy control levels Mismatched double-stranded RNA induces the synthesis of 2 5 A. In turn, 2 5 A binds to and activates native RNase L homodimers that in turn induce apoptosis, removing the anti-apoptotic block, allowing for return of normal cellular functions It is evident from the above results and discussion that relatively simple and rapid methods are provided for diagnosing and/or characterizing chronic immune disease (e.g. MS or CFS) activity in a subject are provided With the subject methods, accurate diagnosis of the chronic immune disease condition, as well the identification of the stage and/or progression of the chronic immune disease condition, may be obtained. As such, the subject methods provide for more accurate diagnostic and/or treatment regimens. In addition, methods of treating hosts for chronic immune disease are provided. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for diagnosing whether a host suffers from a from Chronic Fatigue Syndrome (CFS), said method comprising:

assaying a sample from said host for the presence of at least one low molecular weight RNase L fragment having a molecular weight of from about 35 to about 45 kDal and caspase activity; and if said at least one low molecular weight RNaseL fragment is present, determining that said host suffers from CFS.

2. The method according to claim 1, wherein said sample is a blood cell derived sample.

3. The method according to claim 1, wherein said sample is a PBMC derived sample.

4. A method of diagnosing Chronic Fatigue Syndrome (CFS) activity in a human subject, said method comprising:

(a) obtaining a sample from said subject;

(b) assaying said sample for:
(i) the presence of at least one RNase L fragment having a molecular weight of from about 35 to about 45 kDal; and
(ii) caspase activity if said at least one low molecular weight RNaseL fragment or caspase activity is present, diagnosing CFS activity in said subject.

5. The method according to claim 4, wherein said sample is a blood derived sample.

6. The method according to claim 5, wherein said blood derived sample is derived from PBMCs.

7. The method according to claim 4, wherein said method is a method of confirming whether said subject suffers from CFS.

* * * * *

UNITED STATES PATENT AND TRADEMARK OFFICE
CERTIFICATE OF CORRECTION

PATENT NO. : 6,808,936 B1
DATED : October 26, 2004
INVENTOR(S) : Englebienne, Patrick et al.

It is certified that error appears in the above-identified patent and that said Letters Patent is hereby corrected as shown below:

Column 30,
Line 34, after the word "suffers", delete the words "from a"

Signed and Sealed this

First Day of March, 2005

JON W. DUDAS
*Director of the United States Patent and Trademark Office*